United States Patent
Ohki et al.

[11] Patent Number: 5,899,202
[45] Date of Patent: May 4, 1999

[54] MEDICINE ADMINISTERING DEVICE FOR NASAL CAVITIES AND METHOD OF USING SAME

[75] Inventors: Hisatomo Ohki; Shigemi Nakamura, both of Isesaki; Kazunori Ishizeki, Fujimi; Akira Yanagawa, Yokohama, all of Japan

[73] Assignee: Unisia Jecs Corporation, Atsugi, Japan

[21] Appl. No.: 08/793,337

[22] PCT Filed: Jun. 28, 1996

[86] PCT No.: PCT/JP96/01798

§ 371 Date: Feb. 26, 1997

§ 102(e) Date: Feb. 26, 1997

[87] PCT Pub. No.: WO97/02062

PCT Pub. Date: Jan. 23, 1997

[30] Foreign Application Priority Data

Jun. 30, 1995 [JP] Japan ..................................... 7-188534
Aug. 11, 1995 [JP] Japan ..................................... 7-227265

[51] Int. Cl.⁶ ................................................. A61M 15/08
[52] U.S. Cl. ................. 128/203.22; 604/94; 128/203.15
[58] Field of Search ................... 604/94, 275, 60, 604/61, 69, 70, 58, 59; 128/203.12, 203.15, 203.23, 203.24, 203.18, 203.21, 203.22

[56] References Cited

U.S. PATENT DOCUMENTS

| | | | |
|---|---|---|---|
| 3,874,380 | 4/1975 | Baum | 128/206 |
| 3,906,380 | 9/1975 | Cocozza | 128/266 |
| 5,250,287 | 10/1993 | Cocozza | 424/45 |
| 5,351,683 | 10/1994 | Chiesi et al. | 128/203.12 |
| 5,619,985 | 4/1997 | Ohki et al. | 128/203.21 |
| 5,647,349 | 7/1997 | Ohki et al. | 128/203.15 |
| 5,683,361 | 11/1997 | Elk et al. | 604/58 |
| 5,702,362 | 12/1997 | Herold et al. | 604/58 |
| 5,715,811 | 2/1998 | Ohki et al. | 128/203.15 |
| 5,752,505 | 5/1998 | Ohki et al. | 128/203.15 |
| 5,810,004 | 9/1998 | Ohki et al. | 128/203.15 |

FOREIGN PATENT DOCUMENTS 59-34267  2/1984  Japan .

Primary Examiner—Corrine M. McDermott
Assistant Examiner—Cris L. Rodriguez
Attorney, Agent, or Firm—Foley & Lardner

[57] ABSTRACT

A distance-adjustable nozzle mechanism 25 is disposed to a passage member 17 to be located at the ejection sides of left and right medicine passages 20, 20. The distance-adjustable nozzle distance 25 includes fitting projection sections 26, 26 formed in the passage member 17, adjustable nozzles 27, 27 which are rotatably and detachably attached to the fitting projection sections 26, and tapered spray holes 28, each of which is in communication with the medicine passage 20 and formed throughout the fitting projection section 26, and the adjustable nozzle 27, in which the axis of the adjustable nozzle 27 is eccentric to a rotational center. Accordingly, when each adjustable nozzle 27 is rotated, the nozzles can approach or separate from each other by an amount corresponding to the eccentricity relative to the rotational center, so that the nozzle pitch between the respective adjustable nozzles 27 can be easily adjusted in conformity with the distance between the nasal cavities of the patient. Additionally, cleaning can be facilitated by removing each adjustable nozzle 27.

20 Claims, 14 Drawing Sheets

MEDICINE ADMINISTERING DEVICE FOR NASAL CAVITIES AND METHOD OF USING SAME

FIELD OF THE INVENTION

The present invention relates to a medicine administering device suitable for administering powder-state medicine filled in a medicine accommodating chamber, to nasal cavities, and a method of using the same.

BACKGROUND TECHNIQUE

In general, a method of curing by administering powder-state medicine through nasal cavities has been employed for a patient of nasal allergy, asthma and the like. In this curing method, the powder-state medicine filled in a medicine accommodating chamber, such as a capsule or the like, is administered into nasal cavities by using an exclusive medicine administering device for nasal cavities.

One sprayer to be used for this curing method is shown in Japanese Patent Provisional Publication No. 59-34267.

In the sprayer according to this conventional technique, a cylindrical member is provided at its air inflow-side with a pump section and is formed at its air outflow-side with a concave-shaped section into which a capsule is to be inserted. The cylindrical member is detachably provided at its tip end side with a tip end section, which is formed with an opening section which serves as a medicine spray hole. The tip end section is fitted to the cylindrical member to form a capsule accommodating section. Further, a cap is provided to be detachably fitted to the above-mentioned cylindrical member and the tip end section, and the cap is provided thereinside with an axially extending needle. The cap is fitted to the above-mentioned cylindrical member, thereby forming a hole in the capsule accommodated in the capsule accommodating section with the needle inside the cap.

In this conventional technique, first, the capsule filled with powder-like medicine is inserted in the concave-shaped section of the cylindrical member. Thereafter, the tip end section is fitted to the cylindrical member, thereby accommodating the capsule in the capsule accommodating section. Then, the cap is installed through the tip end section in such a manner that the needle disposed inside the cap pierces the opening section of the tip end section, thereby forming holes at the axially opposite sides of the capsule.

Next, when the medicine is administered, the tip end section is inserted into one of the nasal cavities of the patient, after detaching the cap from the cylindrical member. Then, the pump section is pressed so that air from the pump section streams through an air introduction passage into the capsule. Accordingly, the medicine in the capsule is sprayed through the opening section into the nasal cavities of the patient under the action of this air. Insertion of the tip end section into the nasal cavity is made alternately to both nasal cavities and the pressing action of the pump section is repeated, thereby accomplishing medicine administration to the patient.

Additionally, a clearance is formed between the capsule accommodating section and the capsule so that the medicine administration to nasal cavities is made alternately to the left and right nasal cavities so as to prevent all the medicine in the capsule from being administered after only one pressing action of the pump section. A predetermined amount of the medicine is administered after about four pressing actions of the pump section for each nasal cavity.

Now, in the sprayer according to the above-discussed conventional technique, medicine administration alternates between the left and right nasal cavities, and therefore pressing the pump section and inserting the cylindrical member into each nasal cavity must be repeated many times in order to supply the left and right nasal cavities with an equal amount of the medicine. Accordingly, there is a problem in that treatment during medicine administration becomes cumbersome.

Furthermore, when the hole is formed in the capsule in order to make preparation of the medicine administration, the tip end section is detached from the cylindrical member, and then the capsule is accommodated. Next, the cap is fitted around the above-mentioned cylindrical member and the tip end section, thereby accomplishing the hole formation. When the medicine is to be sprayed, the pump section is operated to accomplish the spraying into the nasal cavities after the cap again is detached. Accordingly, it is required to install and detach the cap, thereby providing such problems in that not only is the preparation action troublesome but also there is the fear of losing the cap.

Furthermore, even if a medicine administering device provided with left and right medicine spraying openings is produced, there is a problem in that it is required to prepare a plurality of kinds of the devices which have different distances between the nasal cavities because the distance between the nasal cavities is different among, for example, children and adults.

The present invention has been made in view of the above-discussed problems of the conventional technique and is intended to provide a medicine administering device for nasal cavities that can administer the medicine in the medicine accommodating chamber simultaneously into the left and right nasal cavities of the patient under simple operations and be used by children and adults.

SUMMARY OF THE INVENTION

A medicine administering device for nasal cavities of the present invention is arranged basically such that a separation-distance between left and right nozzles in left and right directions is adjustable in conformity with a distance between left and right nasal cavities of a patient when powder-like medicine within a medicine accommodating chamber is sprayed from the left and right nozzles respectively into the left and right nasal cavities of the patient under a condition where the powder-like medicine has been accommodated in the medicine accommodating chamber.

Accordingly, when medicine within the medicine accommodating chamber is sprayed from the left and right nozzles respectively into the left and right nasal cavities of the patient, the separation-distance between the nozzle in the left and right directions can be adjusted in conformity with the distance between the nasal cavities of the patient, thereby making it possible to insert the left and right nozzles into the desired positions within the nasal cavities.

Additionally, the present invention comprises a medicine accommodating chamber accommodating therein powder-like medicine, air supply means for supplying air toward the medicine accommodating chamber, passage means including left and right medicine passages through which the medicine in the medicine accommodating chamber is supplied toward left and right nasal cavities of a patient by air supplied from the air supply means, and distance-adjustable nozzle means disposed at an ejection side of the medicine passage of the passage means and adjustable in conformity with a distance between the nasal cavities of the patient in order to spray the medicine under a condition to be inserted into the left and right nasal cavities of the patient.

Accordingly, when air is supplied from the air supply means toward the medicine accommodating chamber under the condition where the medicine has been accommodated within the medicine accommodating chamber, the medicine within the medicine accommodating chamber is simultaneously sprayed to the left and right nasal cavities of the patient from the left and right medicine passages constituting the passage means upon being stirred under the action of air from the air supply means. Additionally, when the distance-adjustable nozzle means is inserted into the left and right nasal cavities of the patient, the distance-adjustable nozzle means is adjusted in conformity with the distance between the left and right nasal cavities of the patient, thereby making it possible to securely insert the distance-adjustable nozzle means into the desired position of the nasal cavity.

Furthermore, the present invention comprises a medicine accommodating chamber accommodating therein powder-like medicine, air supply means for supplying air toward the medicine accommodating chamber, passage means including left and right medicine passages through which the medicine in the medicine accommodating chamber is supplied toward left and right nasal cavities of a patient by air supplied from the air supply means, and distance-adjustable nozzle means including left and right nozzles disposed respectively at ejection sides of medicine passages of the above-mentioned passage means in order to spray the medicine under a state to be inserted respectively in the left and right nasal cavities of the patient, wherein at least one nozzle of the left and right nozzles constituting the distance-adjustable nozzle means is rotatable, and the above-mentioned nozzle is disposed at a position eccentric to a rotational center.

Accordingly, when air is supplied from the air supply means toward the medicine accommodating chamber under the condition where the medicine has been accommodated within the medicine accommodating chamber, the medicine within the medicine accommodating chamber is simultaneously sprayed to the left and right nasal cavities of the patient from the left and right medicine passages constituting the passage means upon being stirred under the action of air from the air supply means. Additionally, when the rotatably disposed nozzle of the left and right nozzles constituting the distance-adjustable nozzle means is rotated, the nozzle turns with a radius corresponding to an eccentric amount. Therefore, by adjusting a rotational amount at this time, the distance between the left and right nozzles is brought into conformity with the distance between the nasal cavities of the patient.

Additionally, the present invention is arranged such that at least one nozzle of the left and right nozzles constituting the distance-adjustable nozzle means is detachable from the above-mentioned passage means.

Accordingly, the respective nozzles and the medicine passages can be sufficiently and easily cleaned by detaching the left and right nozzles from the passage means.

Furthermore, the present invention is arranged such that a spray hole of the nozzle constituting the above-mentioned distance-adjustable nozzle means is formed generally straight.

Accordingly, when the medicine within the medicine accommodating chamber is sprayed into the left and right nasal cavities of the patient, air containing the medicine flows straight from the left and right medicine passages toward the spray holes, so that the air is sprayed into the nasal cavities under its condition to be provided with a straightened flow characteristic and a straight advancing characteristic.

Further, the present invention is arranged such that a spray hole of the nozzle constituting the above-mentioned distance-adjustable nozzle means is formed eccentric.

Accordingly, when the left and right nozzles constituting the distance-adjustable nozzle means are rotated, the eccentric spray holes are rotationally moved together with the respective nozzles, and therefore the spray hole can be positioned at the center of the nasal cavity when each nozzle is inserted into the nasal cavity, so that the medicine can be uniformly sprayed from the spray hole to the inside of the nasal cavity.

Further, the present invention comprises a medicine accommodating chamber accommodating therein powder-like medicine, air supply means for supplying air toward the medicine accommodating chamber, passage means including left and right medicine passages through which the medicine in the medicine accommodating chamber is supplied toward left and right nasal cavities of a patient by air supplied from the air supply means, and distance-adjustable nozzle means including left and right nozzles disposed respectively at ejection sides of medicine passages of the above-mentioned passage means in order to spray the medicine under a state to be inserted respectively in the left and right nasal cavities of the patient, wherein at least one nozzle of the left and right nozzles constituting the distance-adjustable nozzle means is disposed movable in left and right directions relative to the other nozzle.

Accordingly, when air is supplied from the air supply means toward the medicine accommodating chamber under the condition where the medicine has been accommodated within the medicine accommodating chamber, the medicine within the medicine accommodating chamber is simultaneously sprayed to the left and right nasal cavities of the patient from the left and right medicine passages constituting the passage means upon being stirred under the action of air from the air supply means. Additionally, when the movably disposed nozzle of the left and right nozzles constituting the distance-adjustable nozzle means is moved in the left and right directions, the distance between the left and right nozzles can be brought into conformity with the distance between the nasal cavities of the patient.

Further, the present invention is arranged such that the above-mentioned distance-adjustable nozzle means includes a left and right direction guide section for guiding at least one nozzle of the left and right nozzles, and a nozzle holding section for holding the nozzle when the nozzle is moved by the left and right direction guide section.

Accordingly, by moving the one nozzle of the left and right nozzles along the left and right direction guide section, the separation-distance in the left and right directions between it and the other nozzle can be adjusted in conformity with the distance between the nasal cavities, while preventing the nozzles from falling off under the action of the nozzle holding section.

Furthermore, the present invention is arranged such that the adjustable nozzle of the left and right nozzles constituting the above-mentioned distance-adjustable nozzle means and the passage means are connected by a connecting pipe having a flexibility.

Accordingly, since the nozzle and the passage means are connected by the connecting pipe having a flexibility, communication can be always established between the nozzle and the medicine passage of the passage means, allowing the nozzle to move even if the nozzle is moved in left and right directions by virtue of the fact that the connecting pipe can deform in accordance with the moving amount of the nozzle.

Further, the present invention is arranged such that the medicine is supplied into the above-mentioned medicine accommodating chamber by a capsule or a separate supplying tool.

Accordingly, the medicine is supplied to the medicine accommodating chamber by using the capsule or the separate supplying tool, so that a predetermined amount of the medicine can be supplied whenever medicine powder has been administered to the patient.

Additionally, the present invention is arranged such that the above-mentioned air supply means includes means for supplying air by a pump.

Accordingly, when air is discharged from the pump, the discharged air is supplied toward the medicine accommodating chamber.

DETAILED DESCRIPTION OF THE PREFERRED EMBODIMENTS

Hereinafter, a medicine administering device for nasal cavities, according to embodiments of the present invention will be discussed with reference to FIG. 1 to FIG. 18.

First, a first embodiment of the present invention is shown in FIG. 1 to FIG. 8.

Figure 1:
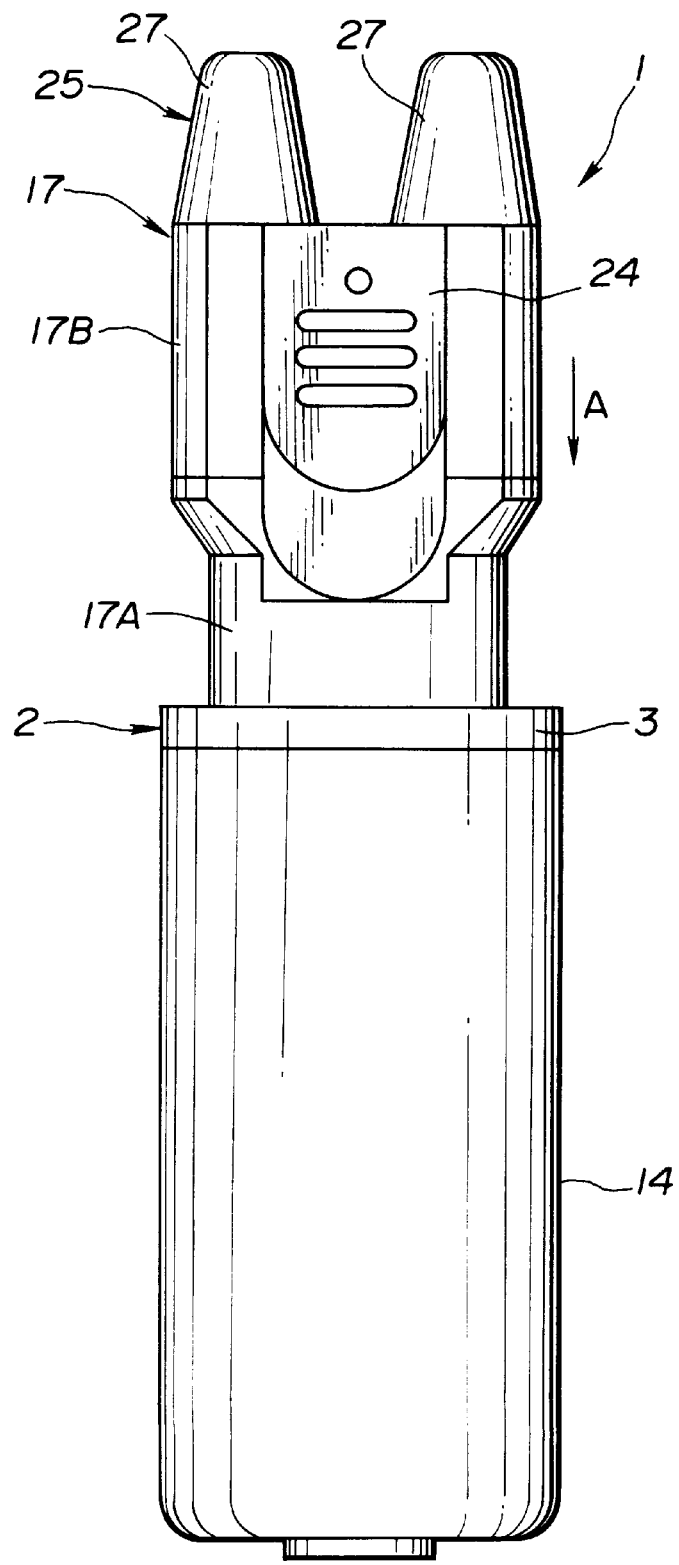
FIG. 1 is a side view showing a medicine administering device for nasal cavities, according to a first embodiment of the present invention.
Figure 2:
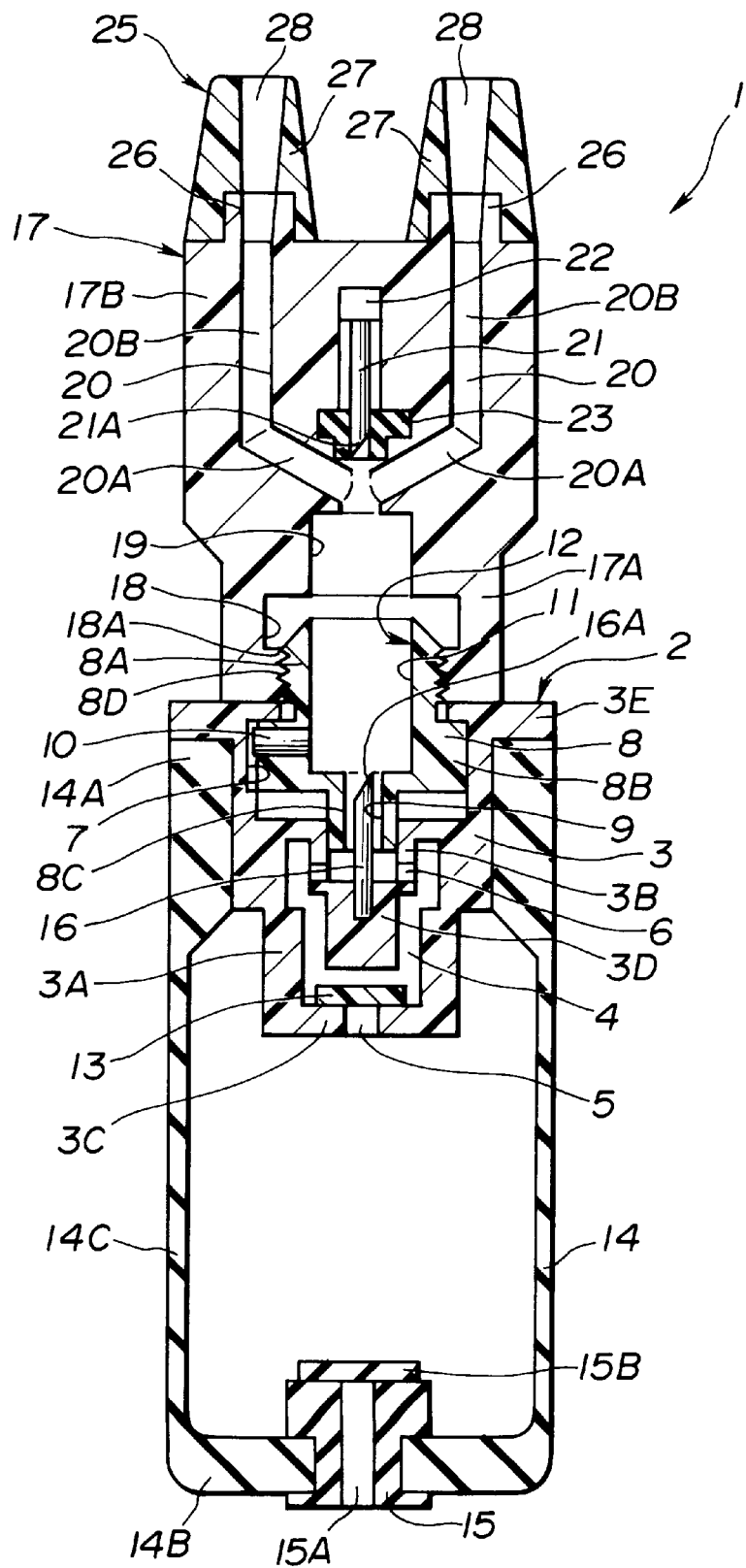
FIG. 2 is a cross-sectional view showing the medicine administering device for nasal cavities, according to the first embodiment of the present invention.

In the drawings, the reference numeral 1 designates the medicine administering device for nasal cavities, according to this embodiment. The medicine administering device 1 for nasal cavities generally comprises a capsule holder 2 discussed after, a pump section 14, a medicine passage 20, and a distance-adjustable nozzle mechanism 25 as shown in FIG. 2.

The above-mentioned capsule holder 2 is arranged to hold a capsule and includes a stationary member 3 which is formed into a double-cylinder shape and will be discussed after, and a movable member 8 which is located at the inner peripheral side of the stationary member 3 and disposed to be axially movable relative to the stationary member 3.

The above-mentioned stationary member 3 generally includes an outer cylindrical section 3A which is formed into the shape of a cylinder with a step, an inner cylindrical section 313 formed inside the outer cylindrical section 3A, a bottom section 3C f-or closing the lower end side of the above-mentioned outer cylindrical section 3A, a medicine trapping section 3D forming a bottom section of the above-mentioned inner cylindrical section 3B, and a flange section 3E formed to be located at the opening side of the above-mentioned outer cylindrical section 3A. The flange section 3E is arranged to prevent the movable member 8, axially movable along the inner peripheral surface of the outer cylindrical section 3A, from coming out and to locate a pump section 14, which is disposed to cover the stationary member 3 from the outer peripheral side. The outer cylindrical section 3A and the inner cylindrical section 3B are arranged such that an opening section of the inner cylindrical section 3B is connected to the outer cylindrical section 3A at the axial intermediate portion so that an air inflow chamber 4 is formed between the cylindrical sections 3A, 3B.

The bottom section 3C of the above-mentioned stationary member 3 is formed with an air supply passage 5 which is in communication with the above-mentioned air inflow chamber 4. The medicine trapping section 3D, serving as the bottom section of the inner cylindrical section 3B, is provided with a first perforating pin 16, which will be discussed after, and is formed projecting toward the side of a one-side capsule hole 11. The inner cylindrical section 3B is formed with communication holes 6, 6 through which the inner peripheral side thereof and the air inflow chamber 4 are in communication with each other, and the outer cylindrical section 3A is formed at its inner peripheral surface with an engaging groove 7 which axially extends to be engagable with a rotation-preventing pin 10 which will be discussed after.

The above-mentioned movable member 8 is disposed axially movable inside the outer-cylindrical section 3A of the stationary member 3, and includes a cylindrical section 8A, a large-diameter bottom section 8B which is disposed at the lower end side of the cylindrical section 8A and axially movably held inside the above-mentioned outer cylindrical section 3A, and a small-diameter projecting section which extends from the central portion of the bottom section 8B into the inner cylindrical section 3B. The cylindrical section 8C is formed with a pin insertion hole 9 which extends in the axial direction thereof and pierces the bottom section 813 to be in communication with the inside of the cylindrical section 8A, in which the first perforating pin 16 passes through the pin insertion hole 9. The cylindrical section 8A is provided at its outer peripheral side with the rotation-preventing pin 10, which is formed projecting radially outwardly. The rotation-preventing pin 10, is to be brought into engagement with the engaging groove 7 of the stationary member 3, thereby allowing the movable member 8 to axially move relative to stationary member 3, and restricting the rotation of the movable member 8 relative to the stationary member 3.

The inner peripheral side of the cylindrical section 8A of the above-mentioned movable member 8 serves as the one-side capsule hole 11 which is incorporated with the other-side capsule hole 19 to constitute a capsule accommodating hole 12 which serves as a medicine accommodating chamber.

Thus, in the capsule holder 2 according to this embodiment, the movable member 8 is arranged to be axially movable along the outer cylindrical section 3A of the stationary member 3. Additionally, when an external thread 8D of the movable member 8 is brought into engagement with an internal thread 18A which will be discussed after, the movable member 8 is automatically raised to the side of a passage member 17 because the rotation of the movable member 8 relative to the stationary member 3 is restricted by the rotation-preventing pin 10.

The reference numeral 13 designates a supply valve disposed inside the air inflow chamber 4. The supply valve 13 is arranged to open and close the air supply passage 5 formed in the stationary member 3, and arranged to make a valve-opening when air is supplied from the pump section 14 and to be seated to close the air supply passage 5 when air is sucked into the pump section 14.

The reference numeral 14 designates a pump section which is formed of a rubber material and formed into the shape of a cylinder with a bottom to serve as air supply means. The pump section 14 includes a thick-wall opening section 14A, a bottom section 14B, and a pressing section 14C located between the opening section 14A and the bottom section 14B. The above-mentioned opening section 14A is installed to the outer cylindrical section 3A of the stationary member 3 to maintain a gas tight seal. Almost all parts of the capsule holder 2 are accommodated inside the pump section 14, by which the medicine administering device 1 for nasal cavities is axially small-sized.

The reference numeral 15 designates a suction valve disposed at the bottom section 14B of the pump section 14. The suction valve 15 generally includes a suction passage 15A which is located at the central portion thereof and in communication with the inside of the pump section 14, and a valve member 15B which opens and closes the suction passage 15A. The valve member 15B makes a valve opening when air is supplied from the pump section 14, and makes a valve closing when air is sucked from the outside into the pump section 14.

The reference numeral 16 designates the first perforating pin provided to the stationary member 3. The first perforating pin 16 has a base end side which is fixed to the medicine trapping section 3D, and a tip end side which is formed into a sharp needle end 16A. The first perforating pin 16 is arranged such that the needle end 16A is projected into the one-side capsule hole 11 when the movable member 8 is located at the side of the pump section 14. Thrusting a capsule K into the one-side capsule hole 11 under this state can form an air inflow hole H1 in the capsule K. When the movable member 8 is located at the side of the passage member 17, the needle end 16A is withdrawn into the pin insertion hole 9, and therefore the needle end 16A is brought into a state to have been extracted from the air inflow hole H1.

The reference numeral 17 designates the passage member which is threaded to the movable member and serves as passage means. The passage member 17 has one side which is located at the side of the capsule holder 2 and forms a small-diameter section 17A, and an other side which forms a large-diameter section 17B. The large-diameter section 17B is provided with the left and right distance-adjustable nozzle mechanism 25.

A movable member threaded hole 18 is formed in the above-mentioned small-diameter section 17A. An internal thread 18A to be engaged with an external thread 8D of the movable member 8 is formed at the inner periphery at the opening side of the movable member threading hole 18. The other-side capsule hole 19 is formed at the innermost part of the movable member threading hole 18, the capsule hole 19 constituting the capsule accommodating hole 12, in cooperation with the one-side capsule hole 11.

The reference numerals 20, 20 designate respectively left and right medicine passages formed in the passage member 17. Each medicine passage 20 includes a branched passage 20A which is in communication with the other-side capsule hole 19 and branched off, and a straight passage section 20B which axially extends from the bifurcated passage 20A, so that the medicine passages are formed generally U-shaped. Each straight passage section 20B is formed at its ejection side into a tapered spray hole 28 which will be discussed after, as shown also in FIG. 3.

The reference numeral 21 designates a second perforating pin which is disposed to be opposite to the first perforating pin 16. The second perforating pin 21 has a base end side which is fixed to a slidable block 22 which is disposed to be axially slidable, and a tip end side which extends to pierce a rubber seal 23 and has a tip end which is formed into a sharp needle end 21A. The above-mentioned slidable block 22 is connected to an operation plate 24 (See FIG. 1) disposed outside the passage member 17 to operate the second perforating pin 21. The second perforating pin 21 is arranged to be moved through the slidable block 22 in the direction indicated by an arrow A by moving the operation plate 24 in a direction indicated by the arrow A, in which an air outflow hole H2 is formed in the capsule K with the needle end 21A of the pin 21.

The reference numeral 25 designates the distance-adjustable nozzle mechanism disposed on the passage member 17. The distance-adjustable nozzle mechanism 25 includes left and right fitting projection sections 26, 26 which are disposed at the side of the passage member 17 and will be discussed after, left and right adjustable nozzles 27, 27 each of which is rotatably installed to each fitting projection section 26, and tapered spray holes 28, 28 each of which is formed throughout each adjustable nozzle 27 and each fitting projection section 26.

The reference numerals 26, 26 designate respectively the left and right fitting projection sections disposed at the upper end surface side of the passage member 17. Each fitting projection 26 is formed into the shape of a cylinder integrally projected from the passage member 17 to cover the ejection side of the straight passage section 20B of the left or right medicine passage 20.

The reference numerals 27, 27 designate respectively the left and right adjustable nozzles which are respectively detachably installed to the fitting projection sections 26, 26. Each adjustable nozzle 27 is to be inserted into the nasal cavity of the patient and formed into the frustoconical shape so that the diameter thereof gradually decreases toward the tip end side of the nozzle 27. The inner periphery of the base end side of the each adjustable nozzle 27 is formed as a fitting hole section 27A which is rotatably and detachably fitted to each fitting projection section 26. Each adjustable nozzle 27 is rotated relative to each fitting projection 26, thereby adjusting a nozzle pitch in conformity with a distance between nasal cavities of the patient for the reasons discussed below.

The reference numerals 28, 28 designate respectively tapered spray holes each of which is formed throughout the inner periphery of each fitting projection 26 and the inner periphery of each adjustable nozzle 27 and gradually spread toward the tip end side. Each tapered spray hole 28 is disposed coaxial with the straight passage section 20B of each medicine passage 20. Each tapered spray hole 28 is arranged such that when air containing the medicine is supplied from each medicine passage 20, this air containing the medicine is flown to gradually spread in a manner to move along the tapered inner wall surface, so that the medicine is administered in a spread manner into the nasal cavities.

Figure 3:
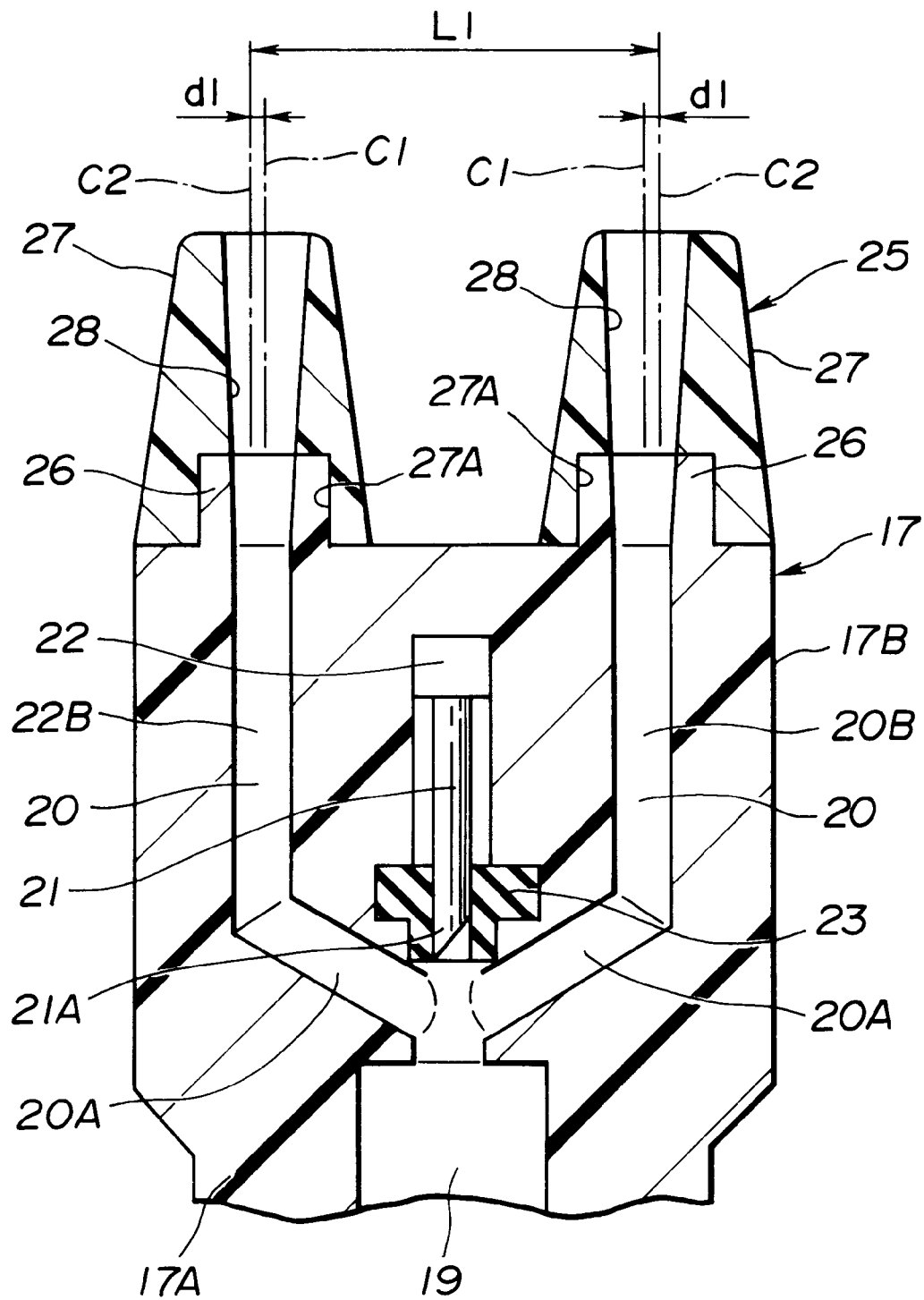
FIG. 3 is an enlarged sectional view of an essential part, showing a distance-adjustable nozzle mechanism at a maximum-separated state.
Figure 4:
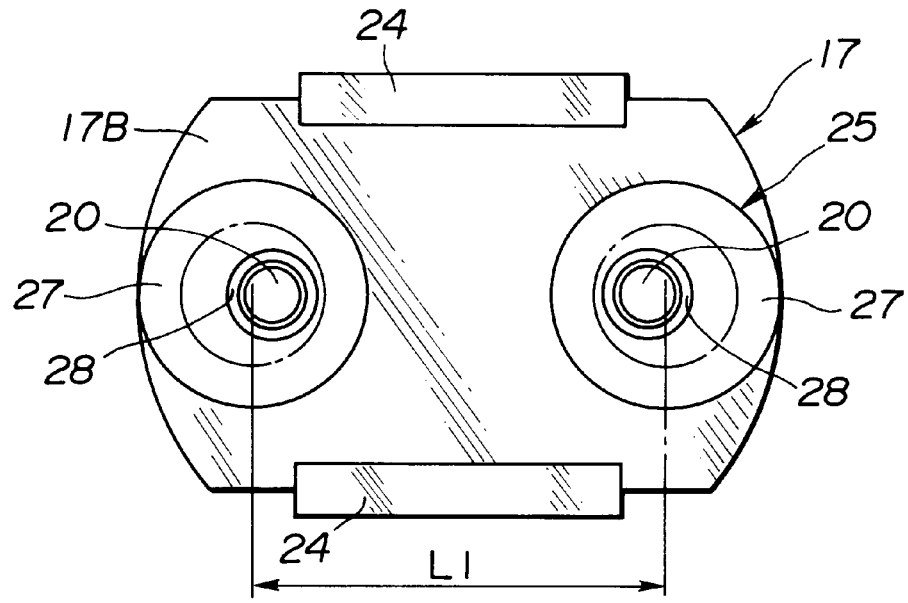
FIG. 4 is a plan view showing the distance-adjustable nozzle mechanism at the maximum-separated state.
Figure 6:
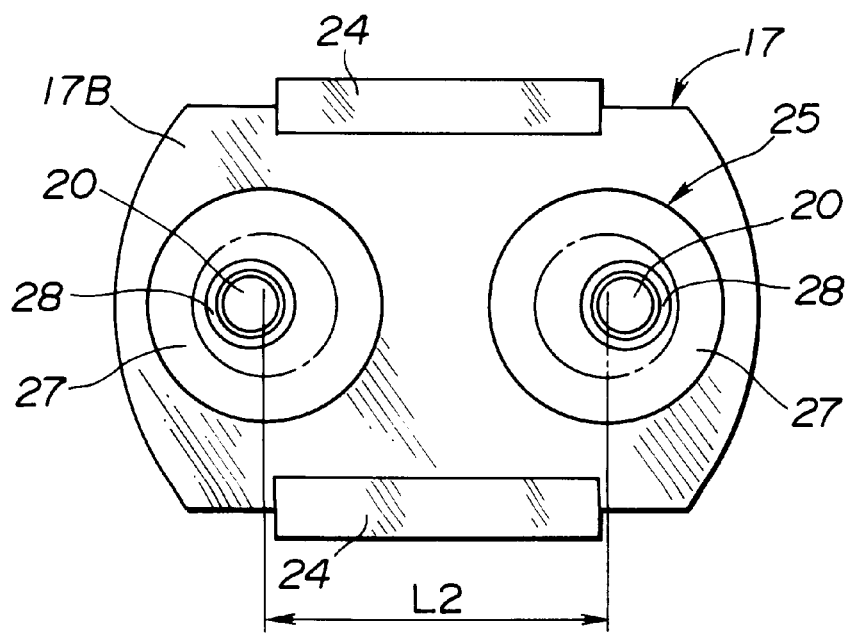
FIG. 6 is a plan view showing the distance-adjustable nozzle mechanism at the minimum and approaching state.
Figure 5:
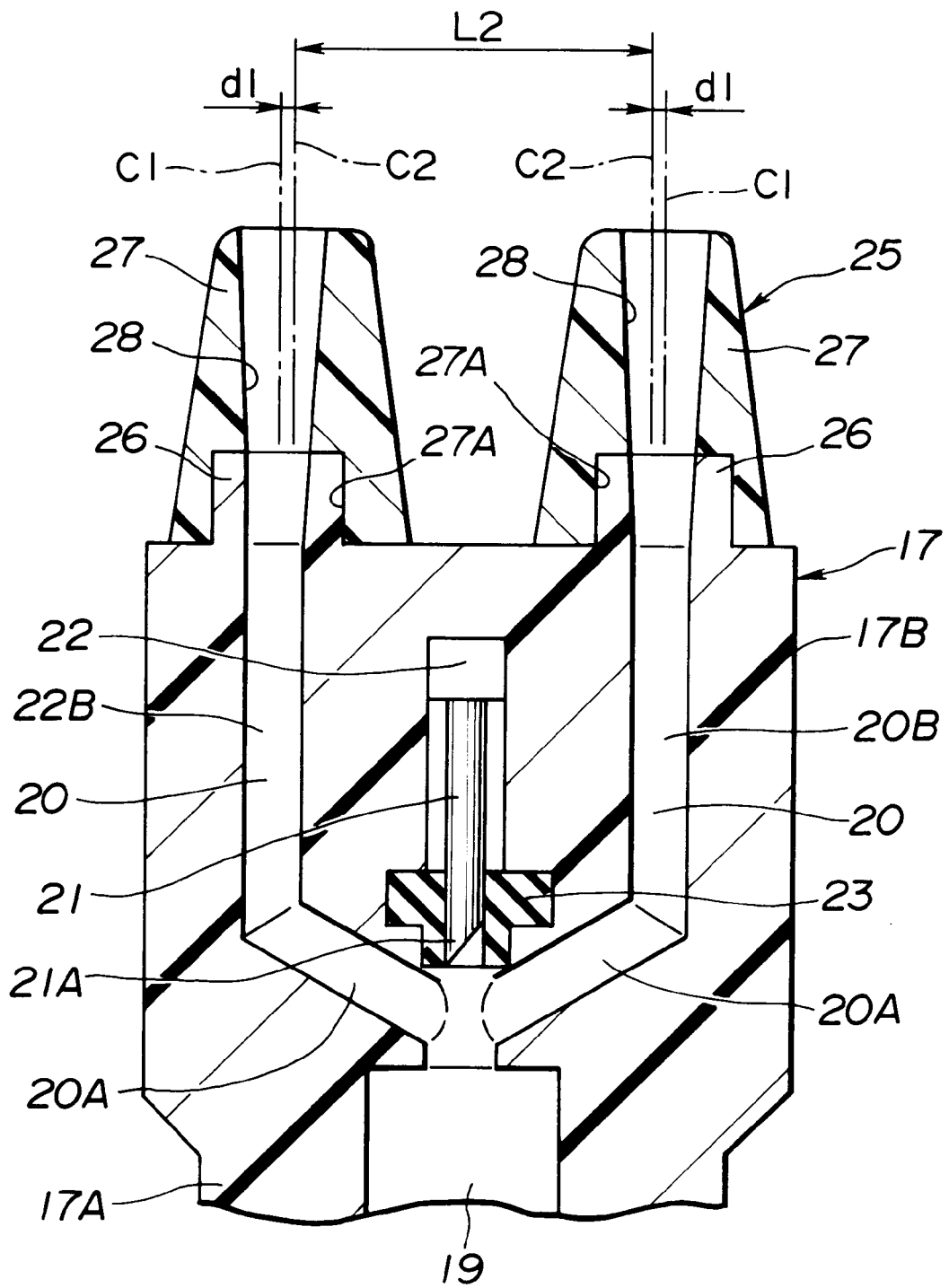
FIG. 5 is an enlarged cross-sectional view showing the distance-adjustable nozzle mechanism at a minimum and approaching state.
Figure 7:
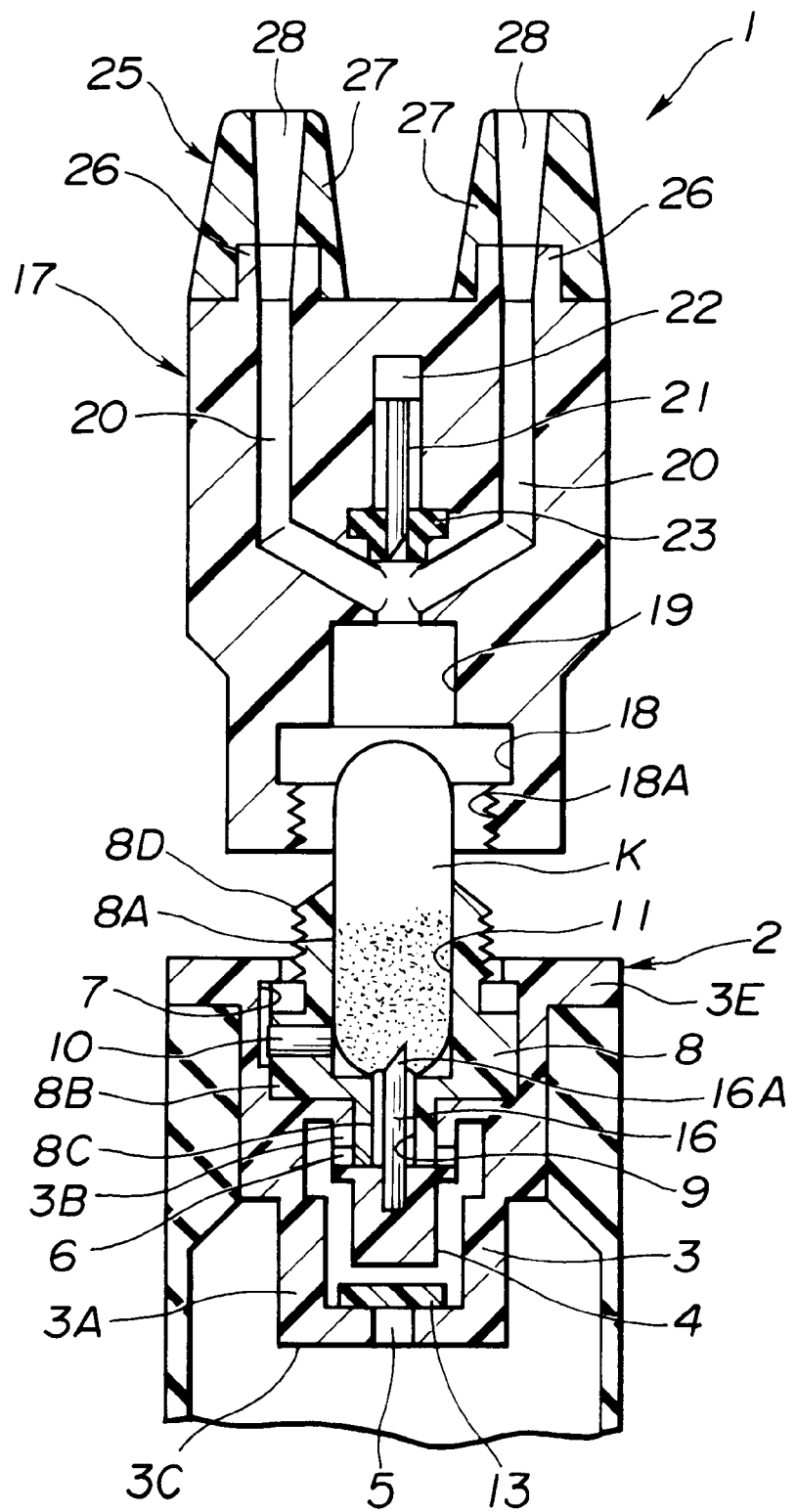
FIG. 7 is a cross-sectional view showing a condition where a passage member is assembled with a capsule holder after an air inflow hole is formed in a capsule by a first perforating pin.

The thus arranged adjustable nozzle mechanism 25 is configured such that each adjustable nozzle 27 is disposed to be rotatable around an axis C1 (as a rotational center) of the straight passage section 20B of the medicine passage 20 and the tapered spray hole 28 as shown in FIG. 3, in which each adjustable nozzle 27 has an axis C2 which is eccentric to or separate from the axis C1 as the rotational center by an eccentric amount d1. Accordingly, by rotating each adjustable nozzle 27, the nozzle pitch between the respective adjustable nozzles 27 becomes L1 at a maximum-separated state as shown in FIGS. 3 and 4, while the nozzle pitch between the respective adjustable nozzles 27 becomes L2 at a minimum and approaching state as shown in FIGS. 5 and 6. As a result, by suitably adjusting the rotational amount of each adjustable nozzle 27, the nozzle pitch can be brought into conformity with the distance between the nasal cavities of the patient.

The medicine administering device for nasal cavities, according to this embodiment has the above-discussed arrangement. Next, its operation will be discussed.

First, the movable member 8 of the capsule holder 2 is located to the side of the pump section 14, so that the needle end 16A of the first perforating pin 16 is brought into a state to be projected into the one-side capsule hole 11. When the capsule K is thrust into the one-side capsule hole 11 in this state, the needle end 16A of the pin 16 is stuck into the capsule K, so that the air inflow hole H1 is formed in the capsule K (See FIG. 7).

Next, in order to assemble the passage member 17 to the capsule holder 2, the internal thread 18A at the side of the passage member 17 is threaded with the external thread 8D at the side of the capsule holder 2. By this, the movable member 8 of the capsule holder 2 moves toward the side of the passage member 17 upon screwing the passage member 17, and therefore the capsule K is maintained in a state to be slightly axially pressed within the capsule accommodating hole 12. At this time, the needle end 16A of the first perforating pin 16 which has formed the air inflow hole H1 in the capsule K is extracted, so that the inside of the capsule K is brought into communication with the air inflow chamber 4 through the pin insertion hole 9 and the respective communication holes 6.

Under this condition, in order to form the air outflow hole H2 in the capsule K, the operation plate 24 is moved in the direction indicated by the arrow A, and therefore the second perforating pin 21 is moved toward the capsule K so that air outflow hole H2 is formed in the capsule K with the needle end 21A of the second perforating pin 21. Thereafter, the operation plate 24 is returned to its original position so that the needle end 21A is extracted from the capsule K. Perforation of the capsule is thus accomplished.

Next, we will discuss a medicine administration operation for spraying into the nasal cavities of the patient the medicine within the capsule that has been perforated.

Figure 8:
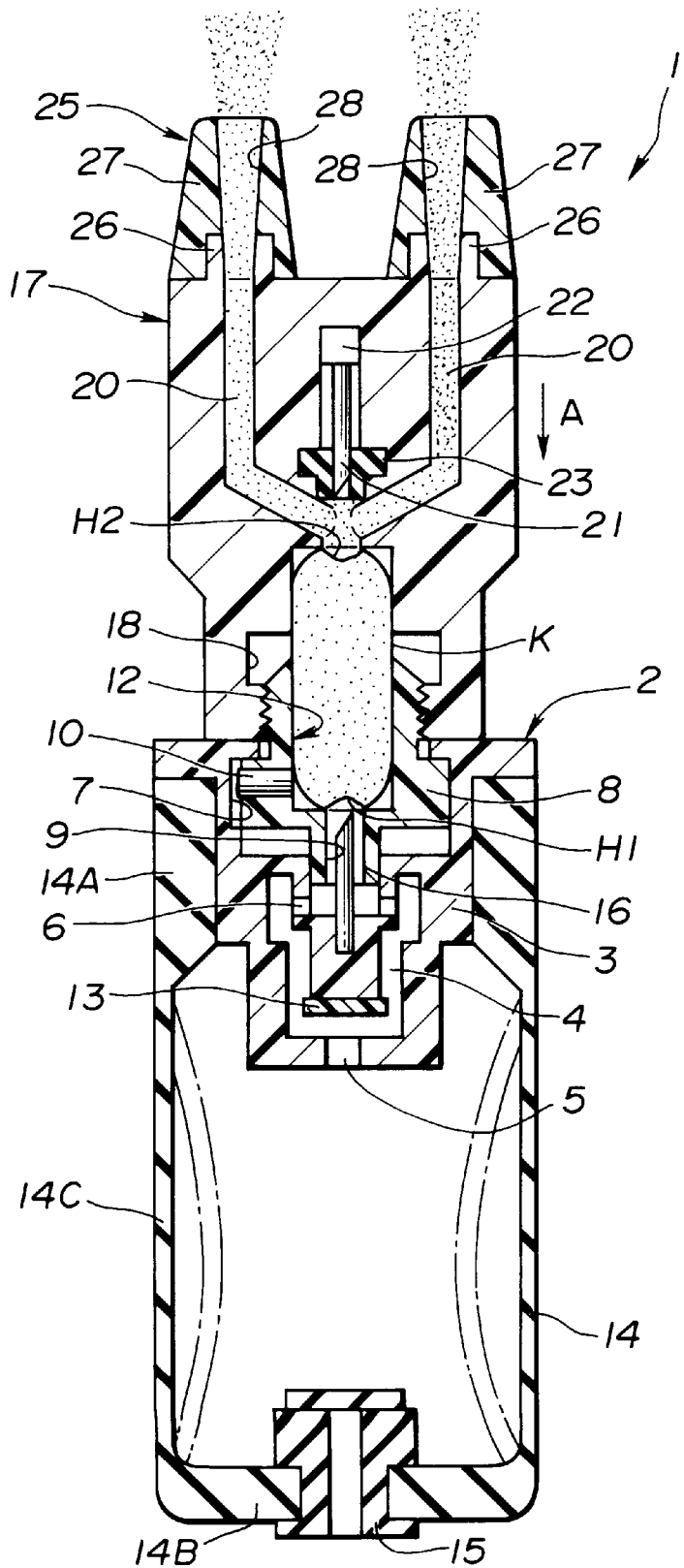
FIG. 8 is a cross-sectional view showing a condition where medicine within the capsule is sprayed by pressing a pump section, as seen from a similar position as that in FIG. 1.

First, the respective adjustable nozzles 27 are inserted into both nasal cavities of the patient, and then the pressing section 14C of the pump section 14 is squeezed as shown in FIG. 8 so that an air stream is generated from the pump section 14. This air moves through the air supply passage 5 so that the supply valve 13 is pressed against the medicine trapping section 3D of the inner cylindrical section 3B to make the valve-opening. Accordingly, the air is flown into the capsule K through the air inflow chamber 4, the respective communication holes 6, the pin-insertion hole 9 and the air inflow hole H1. By this, the air flown into the capsule K stirs the medicine to mix the medicine with the air. This air mixed with the medicine is sprayed from the left and right tapered spray holes 28, 28 through the air outflow hole H2 and the left and right medicine passages 20, 20, so that the medicine can be simultaneously administered into the left and right nasal cavities of the patient.

When the left and right adjustable nozzles 27 are inserted into the left and right nasal cavities of the patient in order to administer the medicine within the capsule K to the patient, each adjustable nozzle 27 is suitably rotated to suitably adjust the nozzle pitch within a range from the nozzle pitch L1 for establishing the maximum-separated state to the nozzle pitch L2 for establishing the minimum and approaching state. As a result, the nozzle pitch between the respective adjustable nozzles 27 can be brought into conformity with the distance between the nasal cavities of the patient, so that the respective adjustable nozzles 27 can be inserted into desired positions in the nasal cavities of the patient securely and smoothly without a feeling of physical disorder.

Thus, according to this embodiment, the air inflow hole H1 and the air outflow hole H2 can be easily formed axially in the capsule K upon installing the capsule K to the movable member 8 and upon once reciprocating axially the second perforating pin 21. As a result, preparing for medicine administration can be largely simplified, and the left and right nasal cavities of the patient can be simultaneously administered since the medicine within the capsule K is sprayed from the left and right adjustable nozzles 27, 27 through the left and right medicine passages 20, 20. Accordingly, treatment ability of the medicine administering device 1 for nasal cavities can be largely improved from the viewpoints of preparation and medicine administration.

Additionally, by rotating each adjustable nozzle 27 in order to insert the respective adjustable nozzles 27 into the nasal cavities of the patient, the nozzle pitch can be very easily brought into conformity with the distance between the nasal cavities within the range from the nozzle pitch L1 for establishing the maximum-separated state to the nozzle pitch L2 for establishing the minimum and approaching state. As a result, each adjustable nozzle 27 can be securely inserted into the desired position within the nasal cavity, so that spray of the medicine into the nasal cavities can be accurately made, thereby improving medicine administration efficiency.

Thus, by causing the locations of the respective adjustable nozzles 27 to be in conformity with the distance of the nasal cavities of the patient, the respective adjustable nozzles 27 can be smoothly inserted into the nasal cavities without a feeling of physical disorder during insertion so that administration can be made under the best condition suitable for each person, while the medicine administering device 1 for nasal cavities can be used in both children and adults which differ in the distance between nasal cavities, thereby largely broadening an application range of the medicine administrating device 1 for nasal cavities. Particularly in this embodiment, the adjustable nozzles 27, 27 are disposed respectively at the left- and right-sides, and therefore an adjusting range of the nozzle pitch can be enlarged, thereby further broadening the application range.

Additionally, since each adjustable nozzle 27 is detachable relative to the passage member 17, each adjustable nozzle 27, the medicine passage 20 and the like can be sufficiently and easily cleaned by removing each adjustable nozzle 27 after the medicine administration, thereby achieving improvements in operationability during cleaning and from a sanitary view point.

In this embodiment, the straight passage section 2013 of each medicine passage 20 is disposed coaxial with the tapered spray hole 28, and therefore air containing the medicine is flown straight through each medicine passage 20 and the tapered spray hole 28, so that this air containing the medicine is provided with straightened flow characteristics and straight advancing characteristics and in an accelerated condition. As a result, the medicine can be supplied to the innermost part of the nasal cavity.

Each medicine passage 20 is provided at its spraying side with each tapered spray hole 28, in which air containing the medicine is spread through each tapered spray hole 28. Accordingly, the medicine can be uniformly administered throughout a wide range of the inside of the nasal cavity of the patient, so that a spraying efficiency of the medicine can be improved, thereby promoting absorption of the medicine to the human body, thus improving effects due to medicine administration.

The medicine administrating device 1 itself houses therein a tool for perforating the capsule K, and therefore the medicine administrating action can be accomplishing without making any removal action. Accordingly, not only attaching and detaching actions for the perforating tool (required by the conventional technique) are omitted, but also there is no fear of losing the perforating tool, thereby rendering treatment of the medicine administrating device safer.

Further, the medicine dropped through the air inflow hole H1 of the capsule-K can be trapped by the medicine trapping section 3D of the stationary member 3, and the medicine trapped by the medicine trapping section 3D is carried by air from the pump section 14 during the medicine administrating action and supplied together with the medicine within the capsule K into the left and right nasal cavities of the patient. As a result, the amount of the medicine to be left in the medicine administrating device 1 for nasal cavities can be reduced so as to securely administer a predetermined amount of the medicine filled within the capsule K to the patient, while reducing the frequency of cleaning of the medicine administrating device 1 for nasal cavities.

Figure 9:
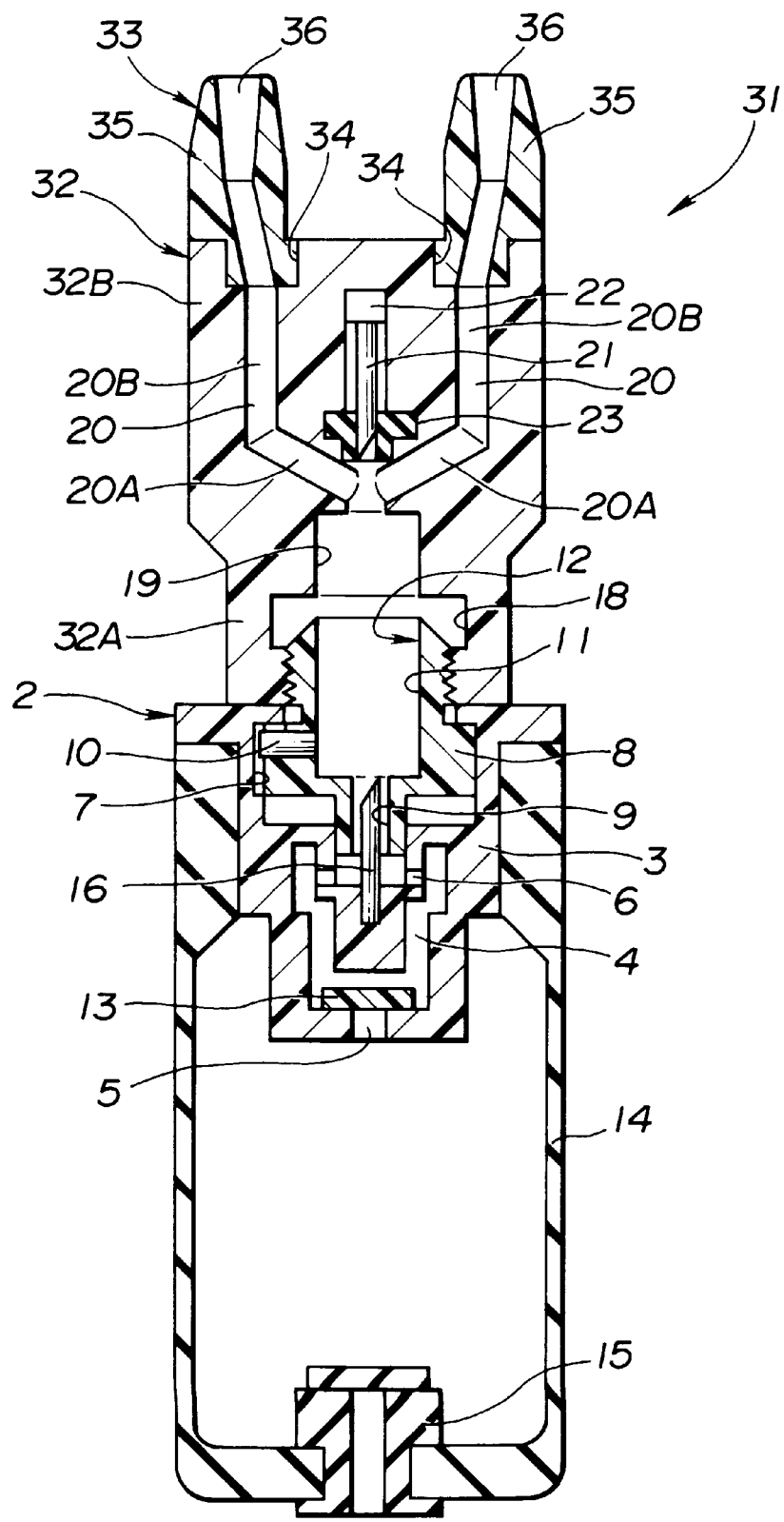
FIG. 9 is a cross-sectional view showing the medicine administering device for nasal cavities, according to the second embodiment of the present invention.
Figure 10:
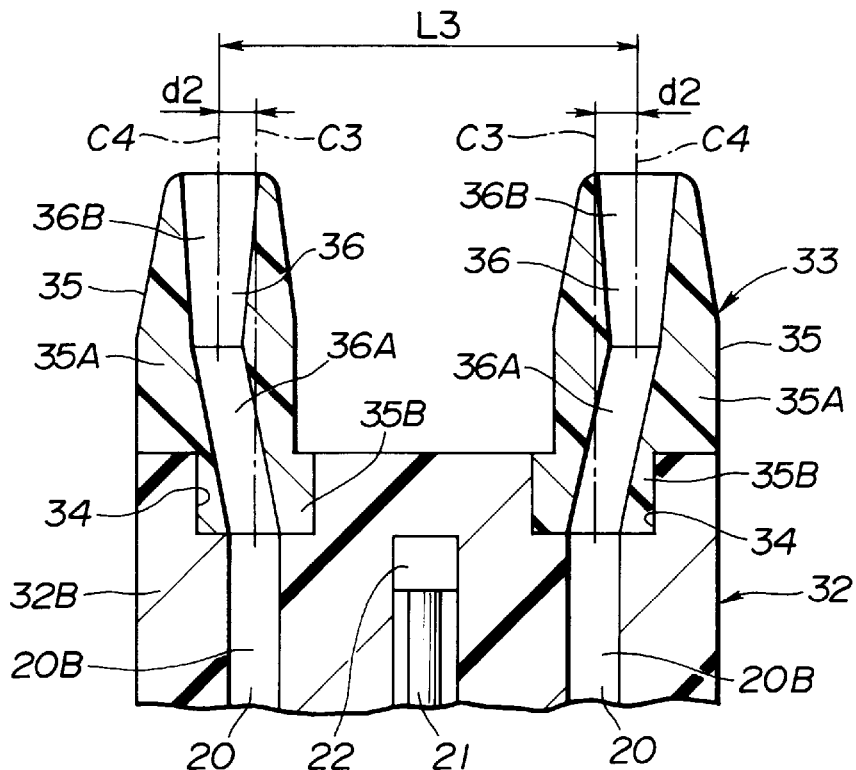
FIG. 10 is an enlarged sectional view of an essential part, showing the distance-adjustable nozzle mechanism at the maximum-separated state.
Figure 11:
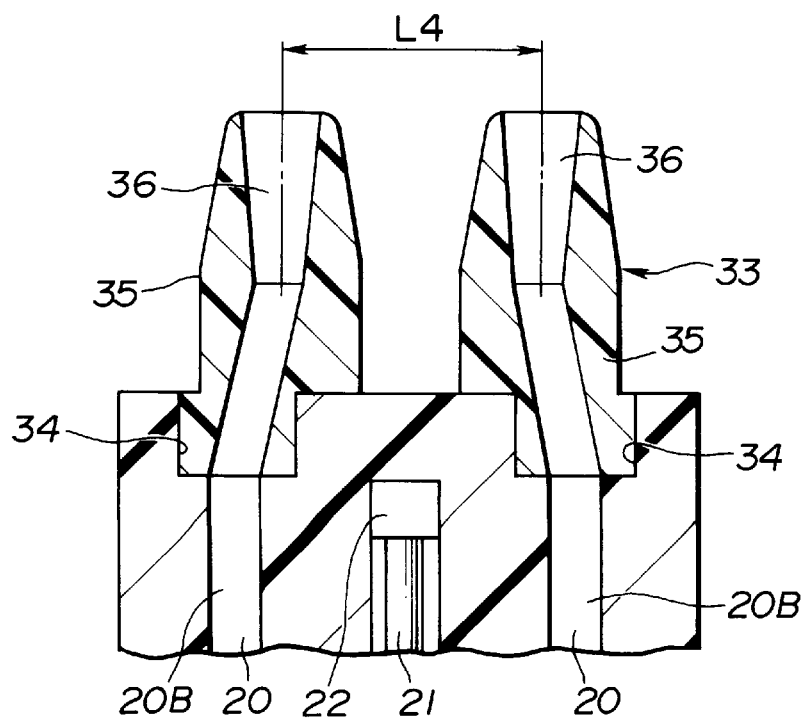
FIG. 11 is an enlarged sectional view of an essential part, showing the distance-adjustable nozzle mechanism at the minimum and approaching state.
Figure 12:
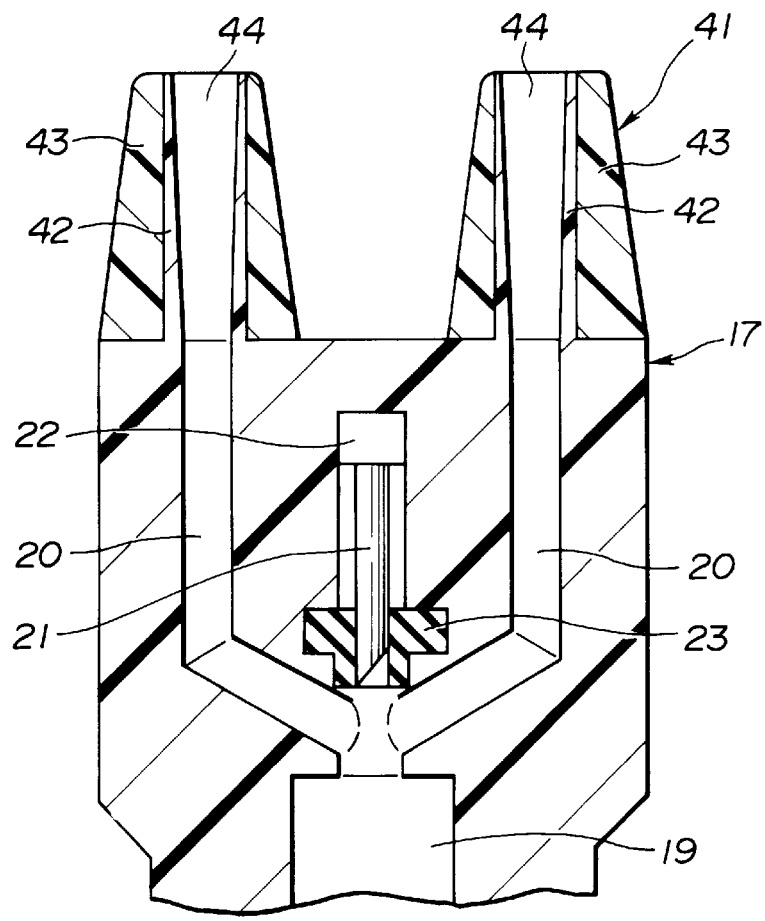
FIG. 12 is a cross-sectional view showing the distance-adjustable nozzle mechanism according to a modified example of the first embodiment of the present invention.

Next, a second embodiment of the present invention is shown in FIGS. 9 to 11. A feature of this embodiment resides in the fact that the spray hole of the adjustable nozzle is disposed eccentric relative to the rotational center. In this embodiment, the same reference numerals are assigned to the same constituent elements as those in the above-mentioned first embodiment and explanation of them is omitted.

In the drawings, the reference numeral 31 designates a medicine administering device for nasal cavities, according to this embodiment. The reference numeral 32 designates a passage member of the medicine administering device 31 for nasal cavities. The passage member 32 includes a small-diameter section 32A and a large-diameter section 32B generally similarly to the passage member 17 discussed in the above-mentioned first embodiment. However, the passage member 32 is different from that of the first embodiment in a point that the large-diameter section 32B is formed at its upper surface side with fitting groove sections 34, 34 which will be discussed after.

The reference numeral 33 designates a distance-adjustable nozzle mechanism. The distance-adjustable nozzle mechanism 33 includes left and right fitting groove sections 34, 34 which are disposed at the side of the passage member 32 and will be discussed after, adjustable nozzles 35, 35 which are respectively rotatably installed to the fitting groove sections 34, and spray holes 36, 36 which are respectively formed in the adjustable nozzles 35.

The reference numerals 34, 34 designate respectively the left and right fitting groove sections. Each fitting groove section 34 is formed at a position corresponding to the left or right medicine passage 20 and formed into the shape of a circular hole. The reference numerals 35, 35 designate respectively the left and right adjustable nozzles according to this embodiment, installed in the left and right fitting groove sections 34, 34. Each adjustable nozzle 35 includes a nasal cavity inserting section 35A whose diameter gradually decreases at it s tip end side to be inserted into the nasal cavity of the patient, and a fitting section 35B which is formed at the base end side of the nasal cavity inserting section 35A and detachably and rotatably fitted in the fitting groove section 34.

Here, the above-mentioned nasal cavity inserting section 35A is arranged to be rotatable around an axis C3 (as a rotational center) of the fitting section 35B. An axis C4 of the nasal cavity inserting section 35A is eccentric relative to or separate from the axis C3 (as the rotational center) by a displacement amount d2. By virtue of this, the nozzle pitch between the respective nasal cavity inserting sections 35A takes L3 at the maximum-separated state as shown in FIG. 10 and L4 at the minimum and approaching state as shown in FIG. 11, upon rotating each adjustable nozzle 35. As a result, the nozzle pitch can be brought into conformity with the distance between the nasal cavities of the patient by suitably adjusting the rotational amount of each adjustable nozzle 35.

The reference numerals 36, 36 designate respectively spray holes which are formed respectively in the adjustable nozzles 35 and formed bent into a generally L-shape. Each spray hole 36 includes an inclined section 36A in communication with the straight passage section 20B of each medicine passage 20, and a tapered section 36B which is in communication with the inclined section 36A and formed coaxial with the nasal cavity inserting section 35A. With this arrangement, when each nasal cavity inserting section 35A is inserted into the nasal cavity, each spray hole 36 is positioned at the central part of the inside of the nasal cavity so that the medicine can be uniformly sprayed into the nasal cavity. Additionally, when air containing the medicine is supplied through each medicine passage 20, each spray hole 36 is arranged such that this air containing the medicine spreads gradually in a manner to move along the inner wall surface of the tapered section 36B, thereby spreading and administering the medicine into the nasal cavity.

Thus, also with this embodiment, it is a matter of course that generally the same effects as those in the above-mentioned first embodiment can be obtained. Particularly in this embodiment, the tapered section 36B of each spray hole 36 is located at the center of (or coaxial with) the nasal cavity inserting section 35A of the adjustable nozzle 35 to be inserted into the patient, so that the medicine can be uniformly sprayed into the nasal cavity through the tapered section 36B. As a result, absorption of the medicine inside the nasal cavity can be further promoted, thereby improving the effects of the medicine.

While the tapered spray hole 28 is formed throughout each fitting projection section 26 and the adjustable nozzle 27 in the above-mentioned first embodiment, the following arrangement may be, for example, employed: Spray cylinders 42, 42 are provided at the upper end surface of the passage member 17, in which adjustable nozzles 43, 43 are respectively rotatably and detachably installed to the outer peripheral sides of the spray cylinders 42, while tapered spray holes 44, 44 are respectively formed at the inner peripheral sides of the above-mentioned spray cylinders 42, like a distance-adjustable nozzle mechanism 41 shown as a modified example in FIG. 12.

Figure 13:
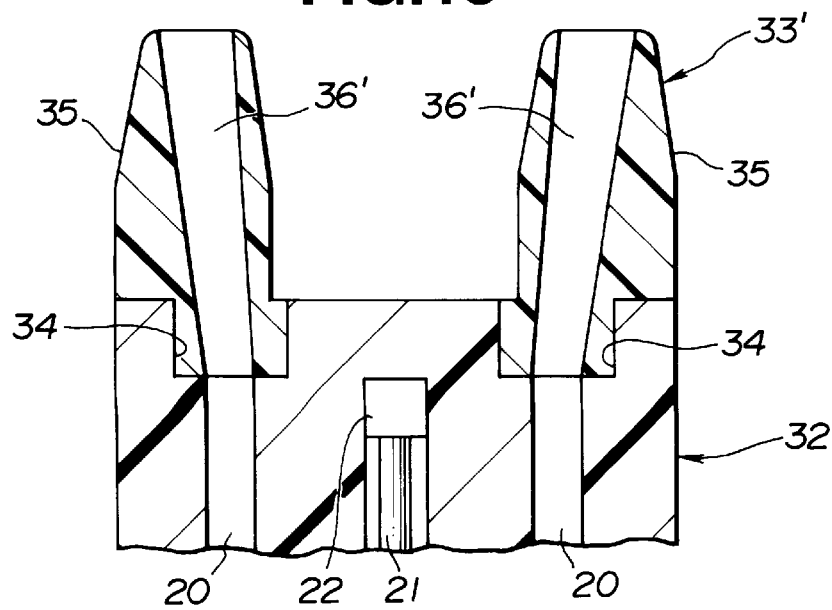
FIG. 13 is a cross-sectional view showing the distance-adjustable nozzle mechanism according to a modified example of the second embodiment of the present invention.
Figure 14:
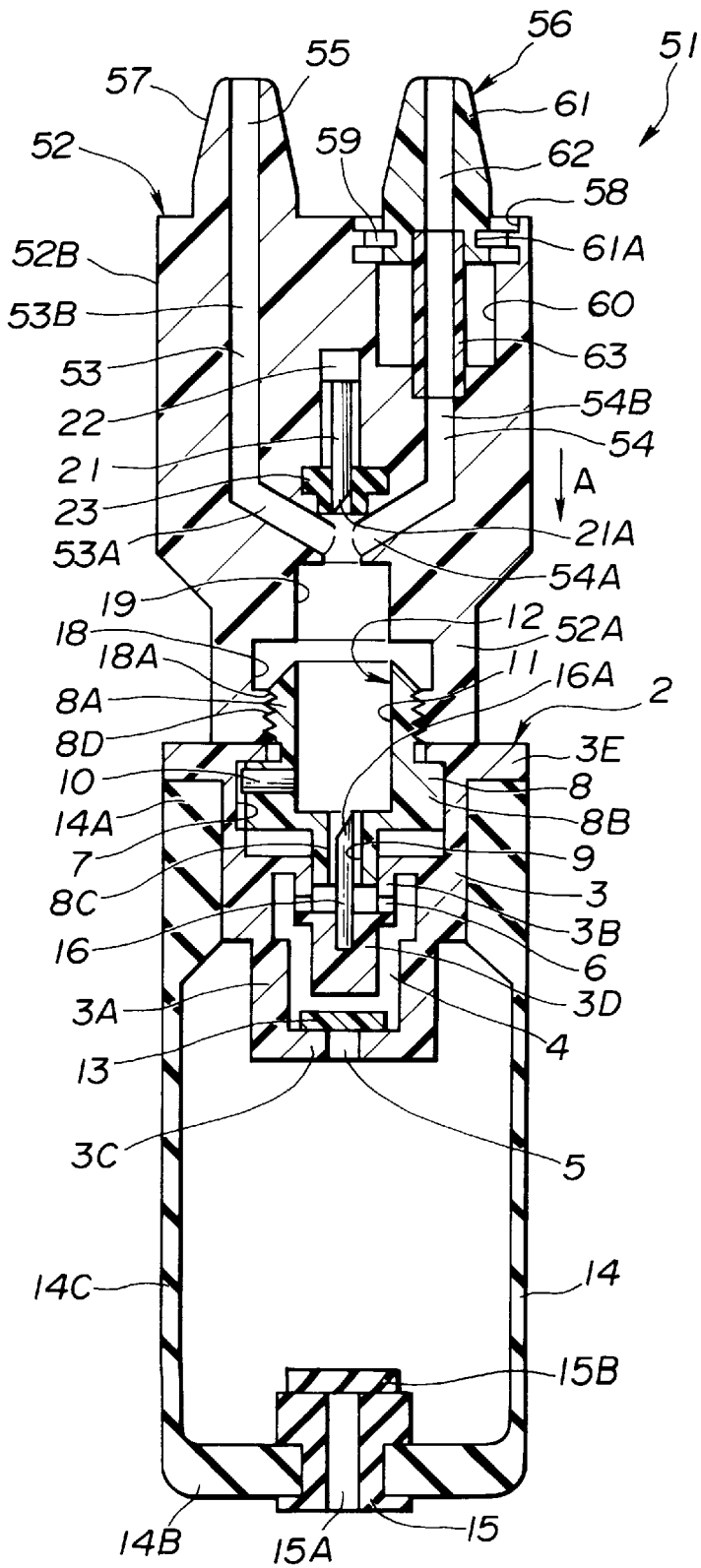
FIG. 14 is a cross-sectional view showing the medicine administering device for nasal cavities, according to a third embodiment of the present invention.

Additionally, the spray hole 36' may be formed straight, extending in each adjustable nozzle 35, like the distance-adjustable nozzle mechanism 33' shown as a modified example the second embodiment in FIG. 13.

While the left and right adjustable nozzles 27, 35, 43 are provided in the above-mentioned first and second embodiments in which the nozzle pitch is adjusted by rotating each adjustable nozzle 27, 35, 43, the following arrangement may be employed: One of the left and right nozzles is a fixed nozzle, while the other one is an adjustable nozzle thereby adjusting the nozzle pitch.

While each adjustable nozzle 27, 35, 43 is arranged to be detachable in the above-mentioned first and second embodiments, each adjustable nozzle may be rotatably fixed, in which each adjustable nozzle can be prevented from being lost.

Next, a third embodiment of the present invention is shown in FIGS. 14 to 18. A feature of this embodiment resides in the fact that the nozzle is arranged to be movable in left and right directions. In this embodiment, the same reference numerals are assigned to the same constituent elements as those in the above-mentioned first embodiment, and explanation of them has been omitted.

In the drawings, the reference numeral 51 designates a medicine administrating device for nasal cavities, according to this embodiment, and the reference numeral 52 designates a passage member as passage means of the medicine administrating device 51 for nasal cavities. The passage member 52 includes a small-diameter section 52A and a large-diameter section 52B generally similarly to the passage member 17 as discussed in the above-mentioned first embodiment. However, the passage member 52 according to this embodiment is different from the first conventional technique in a point that a distance-adjustable nozzle mechanism 56, which will be discussed after, is provided in place of the distance-adjustable nozzle mechanism 25 according to the first embodiment.

The reference numerals 53, 54 designate respectively left and right medicine passages according to this embodiment, formed in the passage member 52. The left and right medicine passages 53, 54 includes respectively branched passages 53A, 54A which are branched off and communicate with the other-side capsule hole 19, straight passage sections 53B, 54B which axially extend respectively from the branched passage sections 53A, 54A, so as to be formed generally U-shaped, in which the ejection side of the left-side straight passage section 53B becomes a spray hole 55 within a fixed nozzle 57, which will be discussed after. Additionally, the right-side straight passage section 54B is short as compared with the left-side straight passage section 53B, and it has an ejection side to which a connecting pipe discussed after is connected.

The reference numeral 56 designates the distance-adjustable nozzle mechanism according to this embodiment, provided in the large-diameter section 52B of the passage member 52. The distance-adjustable nozzle mechanism 56 includes the fixed nozzle, which will be discussed after, a left and right direction guide groove 58, a nozzle holding projection section 59, an adjustable nozzle 61, the connecting pipe 63 and the like.

The reference numeral 57 designates the fixed nozzle which is located at the ejection side of the left-side medicine passage 53 and projected from the large-diameter section 52B of the passage member 52. The fixed nozzle 57 is arranged to be inserted into the nasal cavity of the patient and formed into a frustoconical shape so that its diameter gradually decreases toward its tip end side.

Figure 15:
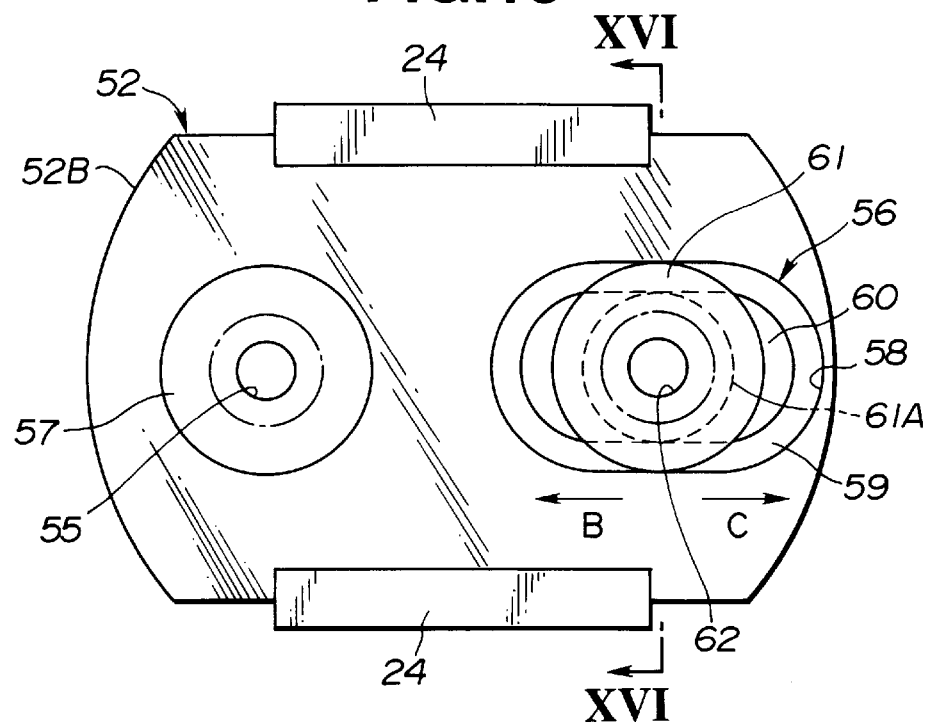
FIG. 15 is a plan view showing the medicine administering device for nasal cavities, according to the third embodiment of the present invention.

The reference numeral 58 designates the left and right direction guide groove formed to open to the other end surface of the large-diameter section 52B of the passage member 52, serving as a left and right direction guide section. The left and right direction guide groove 58 is located on the extension of the straight passage section 54B of the right-side medicine passage 54 and formed into the shape of ellipse, which radially elongates as shown in FIG. 15. The width dimension (the diametrical dimension between the circular arcs) of the left and right direction guide groove 58 is set slightly larger than the diametrical dimension of the adjustable nozzle 61. With this, the adjustable nozzle 61 is movably supported to be movable in the left and right directions (the directions indicated by the arrows B and C).

Figure 16:
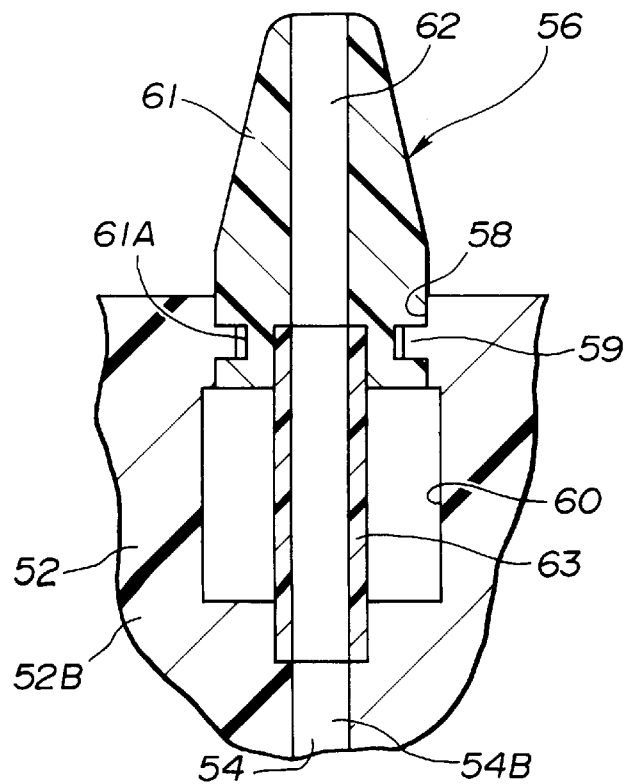
FIG. 16 is a cross-sectional view showing a condition where an adjustable nozzle is fitted to a left and right direction guide groove and to a nozzle holding projection section, as seen from a direction indicated by an arrow XVI—XVI in FIG. 15.

The reference numeral 59 represents a nozzle holding projection section which is disposed within the left and right direction guide groove 58 and serves as a nozzle holding section. The nozzle holding projection section 59 projects from the inner peripheral surface of the left and right direction guide groove 58 and forms a ring-shape as shown in FIG. 16. The nozzle holding projection section 59 is in engagement with the annular groove 61A of the adjustable nozzle 61 and is arranged to hold the adjustable nozzle 61 within the left and right direction guide groove 58 and prevents the adjustable nozzle 61 from falling off.

The reference numeral 60 represents a connecting pipe moving space formed between the straight passage section 54B of the right-side medicine passage 54 and the left and right direction guide groove 58. The connecting pipe moving space 60 is arranged to allow the connecting pipe 63 to move in the left and right directions in accordance with movement of the adjustable nozzle 61.

The reference numeral 61 designates the adjustable nozzle formed projecting from the large-diameter section 52B of the passage member 52. The adjustable nozzle 61 and the fixed nozzle 57 constitute a pair, in which the adjustable nozzle 61 is formed into the frustoconical shape so what its diameter gradually decreases toward its tip end side, generally similarly to the fixed nozzle 57. Additionally, the adjustable nozzle 61 is formed at the outer periphery of its base end side with the annular groove 61A which extends throughout the whole periphery thereof. The adjustable nozzle 61 is in engagement with the nozzle holding projection 59 through the annular groove 61A in a manner to be movable in the left and right directions.

The reference numeral 62 designates the spray hole formed in the adjustable nozzle 61. The spray hole 62 is located at the center of the adjustable nozzle 61 and formed to axially pierce the adjustable nozzle. Additionally, the spray hole 62 is in communication with the right-side medicine passage 54 through the connecting pipe 63.

The reference numeral 63 designates the connecting pipe 63 has a one-end side which is connected to the passage member 17 so as to be in communication with the straight passage section 54B of the right-side medicine passage 54, and an other-end side which is connected to the adjustable nozzle 61 so as to be in communication with the spray hole 62. Additionally, the connecting pipe 63 is made of plastic (resin) material or the like which has a sufficient flexibility. With this, when the adjustable nozzle 61 moves, the connecting pipe 63 deforms in accordance with the amount of movement of the adjustable nozzle, thereby making it possible to always establish communication between the medicine passage 54 and the spray hole 62.

Figure 17:
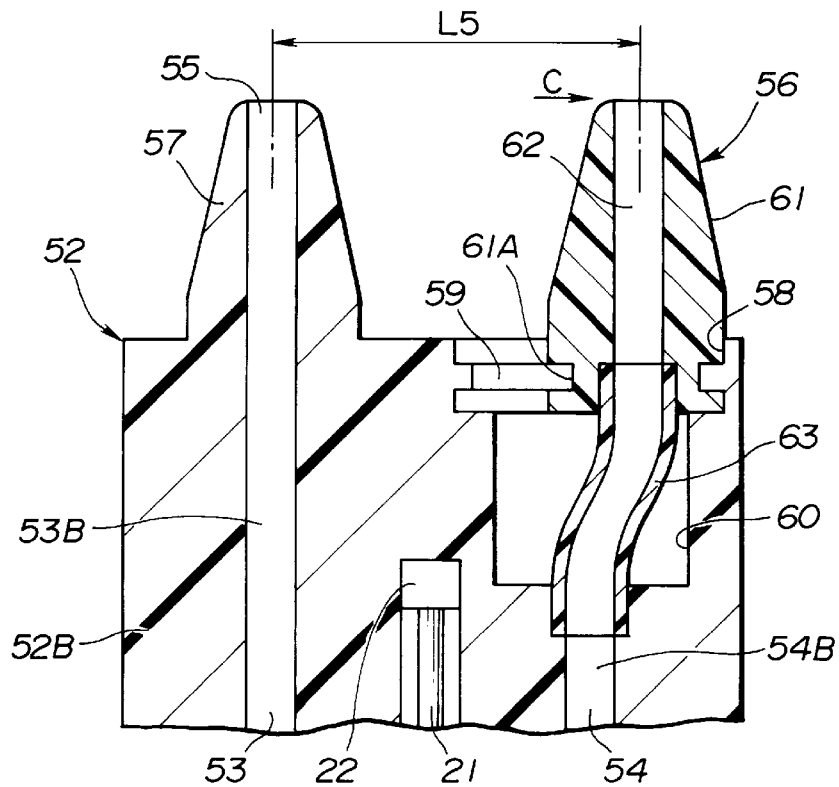
FIG. 17 is an enlarged sectional view of an essential part, showing a condition where the adjustable nozzles are most separated from each other in the left and right directions.
Figure 18:
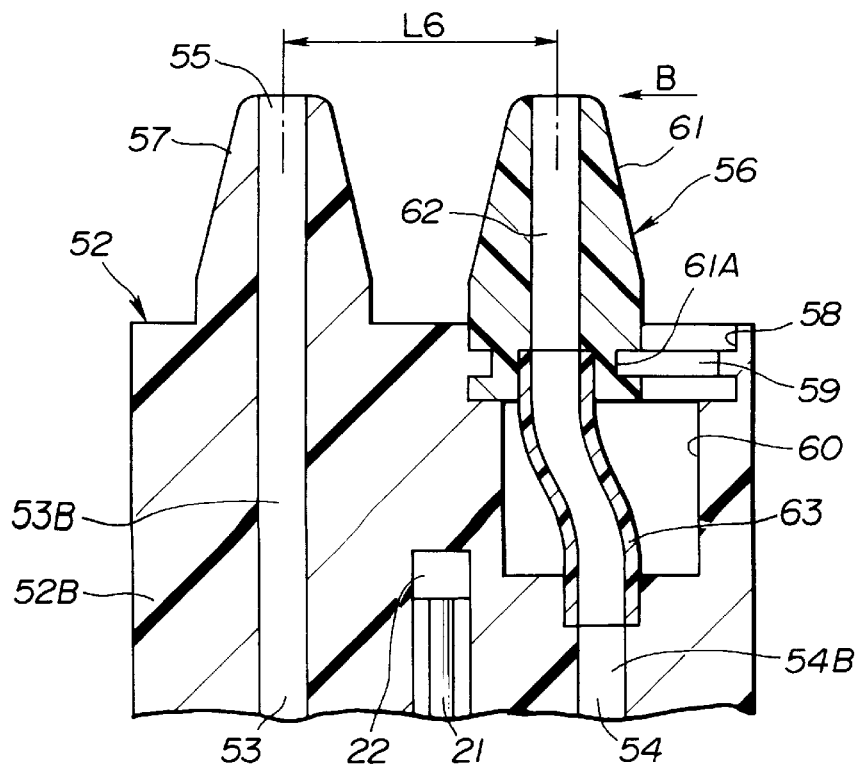
FIG. 18 is an enlarged sectional view of an essential part, showing a condition where the adjustable nozzles are most approached to each other in the left and right directions.

The thus arranged distance-adjustable nozzle mechanism 56 is configured such that the separation-distance (or the nozzle pitch) in the left and right directions of the adjustable nozzle 61 and the fixed nozzle 57 can be L5 for establishing the maximum-separated state by moving the adjustable nozzle 61 in the direction indicated by the arrow B as shown in FIG. 17, while the nozzle pitch can be L6 for establishing the minimum and approaching state by moving the adjustable nozzle 61 in the direction indicated by the arrow C as shown in FIG. 18. Accordingly, the nozzle pitch between the fixed nozzle 57 and the adjustable nozzle 61 can be brought into conformity with the distance between the nasal cavities of the patient by moving the adjustable nozzle 61 in the directions indicated by the arrows B and C and by suitably adjusting the nozzle pitch within a range of from L5 for the maximum-separated state to L6 for the minimum and approaching state. Since the adjustable nozzle 61 is installed within the left and right direction guide groove 58 so that the annular groove 61A is in engagement with the nozzle holding projection section 59, the adjustable nozzle 61 can be prevented from falling off from the passage member 17.

Thus, also with this embodiment, generally the same effects as those in the above-mentioned respective embodiments can be obtained. Particularly in this embodiment, by moving the adjustable nozzle 61 in the left and right directions along the left and right direction guide groove 58, the separation-distance (or the nozzle pitch) in the left and right directions of the adjustable nozzle and the fixed nozzle 57 can be brought into conformity with the distance between the nasal cavities of the patient within the range from L5 for the maximum-separated state to L6 for the minimum and approaching state, thereby further facilitating adjustment of the nozzle pitch.

Additionally, the nozzle holding projection section 59 is formed within the direction guide groove 58, in which the nozzle holding projection section 59 is in engagement with the annular groove 61A of the adjustable nozzle 61. As a result, the adjustable nozzle 61 can smoothly move along the nozzle holding projection section 59, and the adjustable nozzle 61 can be prevented from falling off from the passage member 52.

Further, the right-side medicine passage 54 and the spray hole 62 are in communication with each other through the connecting pipe 63 made of the flexible material, and therefore the medicine passage 54 and the spray hole 62 can be always in communication with each other, so that the medicine can be accurately sprayed from the spray hole 62 toward the inside of the nasal cavities.

Figure 19:
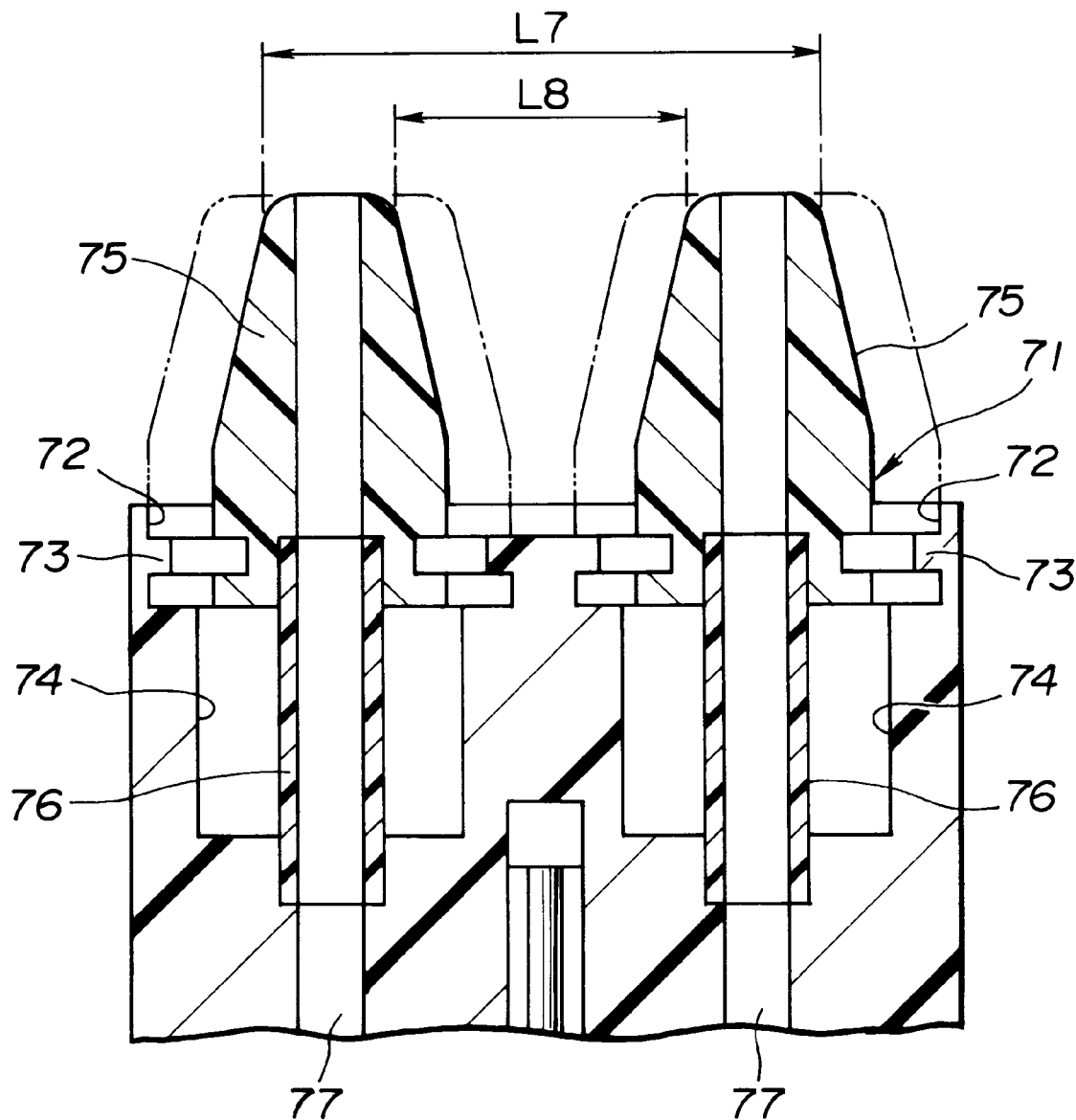
FIG. 19 is a cross-sectional view showing the distance-adjustable nozzle mechanism according to a modified example of the third embodiment.

In the above-mentioned third embodiment, the distance-adjustable nozzle mechanism is arranged such that the left-side one of the left and right nozzles is the fixed nozzle while the right-side one is the adjustable nozzle 61, so that the adjustable nozzle 61 is configured to be approached or separated relative to the fixed nozzle 57, thereby adjusting the nozzle pitch. However, the distance-adjustable nozzle mechanism 56 may arranged for example such that, like a distance-adjustable nozzle mechanism 71 shown as a modified example in FIG. 19, left and right direction guide grooves 72, 72, nozzle holding projection sections 73, 73, and connecting pipe moving spaces 74, 74 may be provided at the left and right sides, in which adjustable nozzles 75, 75 are movably fitted respectively to the left and right holding guide grooves 72, 72, while the adjustable nozzles 75, 75 are connected respectively to the medicine passages 77, 77 through the connecting pipes 76, 76.

In this case, by moving the one-side adjustable nozzle 75 relative to the other-side adjustable nozzle 75, the nozzle pitch can be suitably adjusted similarly to the third embodiment. Additionally, in this second modified example, the respective adjustable nozzles 75 approach or separate relative to each other, thereby allowing the nozzle pitch to take L7 at the maximum-separated state and L8 at the minimum and approached state, so that the nozzle pitch can be adjusted within a range which is two times that in the above-mentioned third embodiment thus extending the application range.

In the first embodiment, the tapered spray hole 28, 44 has been exemplified as the spray hole. In the second embodiment, the spray hole 36 having the tapered section 36B has been exemplified as the spray hole. In the third embodiment, the spray hole 56, 62 is straight and has the same diameter along its axis. However, the spray hole is not limited to these, so that it is preferable to suitably change the shape of the spray hole in accordance with the spray condition of the medicine.

In the above-mentioned third embodiment, explanation has been made for an example in which the ellipse-shaped left and right direction guide groove 58 is formed as the left and right direction guide section, in which the adjustable nozzle 61 is fitted in the left and right direction guide groove 58. However, a left and right guide projection section may be provided as the left and right direction guide section, in which the adjustable nozzle is slidably fitted to the left and right direction guide projection.

In the above-mentioned third embodiment, the nozzle holding projection section 59 and the annular groove 61A in the adjustable nozzle 61 are formed so that the nozzle holding projection 59 and the annular groove 61A are in engagement with each other. However, a nozzle guide may be formed as a depressed groove while the adjustable nozzle may be formed with a projection section to be engaged with the depressed groove.

In the above-mentioned respective embodiments, the capsule accommodating hole 12 is formed as the medicine accommodating chamber, in which a capsule K stores medicine and is inserted in the capsule accommodating hole 12. However, the medicine may be supplied directly into the medicine accommodating chamber from the outside by using a separate supplying tool or the like. In this case, the capsule is not required.

As discussed above, the medicine administering device for nasal cavities, according to the present invention and a method of using the same, can be applied to devices in which fine powder, granule or the like filled in a capsule can be inhaled upon breaking the capsule.

We claim:

1. A medicine administering device for nasal cavities, comprising:

left and right nozzles, at least one nozzle being adjustable in one of a left and a right direction in conformity with a distance between left and right nasal cavities of a patient; and a medicine accommodating chamber for containing medicine and communicating with the left and right nozzles for spraying the medicine respectively into the left and right nasal cavities of the patient.

2. The medicine administering device for nasal cavities, as claimed in claim 1, further comprising a supplying tool for supplying medicine into the medicine accommodating chamber.

3. The medicine administering device for nasal cavities, as claimed in claim 1, further comprising:

air supply means for supplying air toward the medicine accommodating chamber; and left and right medicine passages through which the medicine in the medicine accommodating chamber is supplied toward the left and right nasal cavities of the patient by air supplied from the air supply means, the left and right medicine passages each having an ejection side opposite the air supply means;

wherein the left and right nozzles are disposed respectively at the ejection sides of the left and right medicine passages.

4. The medicine administering device for nasal cavities, as claimed in claim 3, further comprising:

a left and right direction guide section for guiding the at least one nozzle of the left and right nozzles; and a nozzle holding section for holding the at least one nozzle when the at least one nozzle is moved by the left and right direction guide section.

5. The medicine administering device for nasal cavities, as claimed in claim 4, wherein the at least one nozzle of the left and right nozzles and a respective one of the left and right medicine passages are connected by a flexible connecting pipe.

6. The medicine administering device for nasal cavities, as claimed in claim 3, wherein the at least one nozzle of the left and right nozzles and a respective one of the left and right medicine passages are connected by a flexible connecting pipe.

7. The medicine administering device for nasal cavities, as claimed in claim 3, further comprising a supplying tool for supplying medicine into the medicine accommodating chamber.

8. The medicine administering device for nasal cavities, as claimed in claim 3, wherein said air supply means includes an air pump.

9. The medicine administering device for nasal cavities, as claimed in claim 1, wherein a method of using the medicine administering device for nasal cavities comprises:

adjusting a separation distance of the left and right nozzles by at least one of (a) rotating the at least one nozzle of the left and right nozzles so as to cause the at least one nozzle of the left and right nozzles to be eccentric relative to an other of the left and right nozzles and (b) slidably moving the at least one nozzle of the left and right nozzles in the left and right directions relative to the other nozzle.

10. A medicine administering device for nasal cavities, comprising:

a medicine accommodating chamber for accommodating therein medicine;

air supply means for supplying air toward the medicine accommodating chamber;

left and right medicine passages through which the medicine in the medicine accommodating chamber is supplied toward left and right nasal cavities of a patient by air supplied from the air supply means, the left and right medicine passages each having an ejection side opposite the air supply means; and distance-adjustable nozzle means disposed at the ejection side of at least one of the left and right medicine passages and adjustable in conformity with a distance between the nasal cavities of the patient.

11. The medicine administering device for nasal cavities, as claimed in claim 10, further comprising a supplying tool for supplying medicine into the medicine accommodating chamber.

12. The medicine administering device for nasal cavities, as claimed in claim 10, wherein said air supply means includes an air pump.

13. A medicine administering device for nasal cavities, comprising:

a medicine accommodating chamber for accommodating therein;

air supply means for supplying air toward the medicine accommodating chamber;

left and right medicine passages through which the medicine in the medicine accommodating chamber is supplied toward left and right nasal cavities of a patient by air supplied from the air supply means, the left and right medicine passages each having an election side opposite the air supply means; and left and right nozzles disposed respectively at the ejection sides of the left and right medicine passages, wherein at least one nozzle of the left and right nozzles is rotatable, and the nozzle is disposed at a position eccentric to a rotational center.

14. The medicine administering device for nasal cavities, as claimed in claim 13, wherein the at least one nozzle of the left and right nozzles is detachable from a respective one of the left and right medicine passages.

15. The medicine administering device for nasal cavities, as claimed in claim 14, wherein the at least one nozzle of the left and right nozzles has a spray hole is generally straight.

16. The medicine administering device for nasal cavities, as claimed in claim 14, wherein the at least one nozzle of the left and right nozzles has a spray hole that is eccentric.

17. The medicine administering device for nasal cavities, as claimed in claim 13, wherein the at least one nozzle of the left and right nozzles has a spray hole is generally straight.

18. The medicine administering device for nasal cavities, as claimed in claim 13, wherein the at least one nozzle of the left and right nozzles has a spray hole that is eccentric.

19. The medicine administering device for nasal cavities, as claimed in claim 13, further comprising a supplying tool for supplying medicine into the medicine accommodating chamber.

20. The medicine administering device for nasal cavities, as claimed in claim 13, wherein said air supply means includes an air pump.

* * * * *

UNITED STATES PATENT AND TRADEMARK OFFICE
CERTIFICATE OF CORRECTION

PATENT NO. : 5,899,202
DATED : May 4, 1999
INVENTOR(S) : Hisatomo OHKI et al.

It is certified that error appears in the above-identified patent and that said Letters Patent is hereby corrected as shown below:

On the title page, delete item [73] in its entirety and substitute therefor --[73] Assignee: UNISIA JECS CORPORATION, Atsugi, Japan; and DOTT LIMITED COMPANY, Yokohama-Shi, Japan.--

Signed and Sealed this

Twenty-fifth Day of January, 2000

Attest:

Attesting Officer

*Acting Commissioner of Patents and Trademarks*